United States Patent
Costello et al.

(10) Patent No.: US 11,576,588 B2
(45) Date of Patent: Feb. 14, 2023

(54) METHOD OF USING LUNG AIRWAY CARINA LOCATIONS TO IMPROVE ENB REGISTRATION

(71) Applicant: Covidien LP, Mansfield, MA (US)

(72) Inventors: David M. Costello, Delano, MN (US); Lev A. Koyrakh, Plymouth, MN (US); Michael E. Calcutt, Burnsville, MN (US)

(73) Assignee: Covidien LP, Mansfield, MA (US)

( * ) Notice: Subject to any disclaimer, the term of this patent is extended or adjusted under 35 U.S.C. 154(b) by 302 days.

(21) Appl. No.: 16/913,204

(22) Filed: Jun. 26, 2020

(65) Prior Publication Data

US 2020/0323463 A1 Oct. 15, 2020

Related U.S. Application Data

(63) Continuation of application No. 15/296,141, filed on Oct. 18, 2016, now Pat. No. 10,709,352.

(Continued)

(51) Int. Cl.
*A61B 5/00* (2006.01)
*A61B 5/06* (2006.01)
(Continued)

(52) U.S. Cl.
CPC ............ *A61B 5/066* (2013.01); *A61B 1/2676* (2013.01); *A61B 5/08* (2013.01); *A61B 6/032* (2013.01);
(Continued)

(58) Field of Classification Search
CPC combination set(s) only.
See application file for complete search history.

(56) References Cited

U.S. PATENT DOCUMENTS 5,592,939 A 1/1997 Martinelli
5,611,025 A 3/1997 Lorensen et al.
(Continued)

FOREIGN PATENT DOCUMENTS

JP 2012514738 6/2012

OTHER PUBLICATIONS

European Examination Report issued in corresponding Appl. No. EP 16195857.4 dated Jan. 12, 2021 (3 pages).

(Continued)

*Primary Examiner* — Joel F Brutus
(74) *Attorney, Agent, or Firm* — Weber Rosselli & Cannon LLP

(57) ABSTRACT

Disclosed are systems, devices, and methods for registering a luminal network to a 3D model of the luminal network. An example method comprises generating a 3D model of a luminal network, identifying a target within the 3D model, determining locations of a plurality of carinas in the luminal network proximate the target, displaying guidance for navigating a location sensor within the luminal network, tracking the location of the location sensor, comparing the tracked locations of the location sensor and the portions of the 3D model representative of open space, displaying guidance for navigating the location sensor a predetermined distance into each lumen originating at the plurality of carinas proximate the target, tracking the location of the location sensor while the location sensor is navigated into each lumen, and updating the registration of the 3D model with the luminal network based on the tracked locations of the location sensor.

18 Claims, 4 Drawing Sheets

Related U.S. Application Data

(60) Provisional application No. 62/246,721, filed on Oct. 27, 2015.

(51) Int. Cl.

| | | |
|---|---|---|
| *A61B 10/04* | (2006.01) | |
| *A61B 34/20* | (2016.01) | |
| *A61B 1/267* | (2006.01) | |
| *A61B 5/08* | (2006.01) | |
| *A61B 6/03* | (2006.01) | |
| *A61B 6/00* | (2006.01) | |
| *A61B 17/00* | (2006.01) | |
| *A61B 90/00* | (2016.01) | |
| *A61B 34/10* | (2016.01) | |

(52) U.S. Cl.
CPC ........... *A61B 6/5217* (2013.01); *A61B 10/04* (2013.01); *A61B 34/20* (2016.02); *A61B 6/466* (2013.01); *A61B 2017/00809* (2013.01); *A61B 2034/105* (2016.02); *A61B 2034/2051* (2016.02); *A61B 2090/363* (2016.02); *A61B 2090/365* (2016.02); *A61B 2090/367* (2016.02); *A61B 2090/3762* (2016.02); *A61B 2090/3925* (2016.02)

(56) References Cited

U.S. PATENT DOCUMENTS

| | | |
|---|---|---|
| 5,676,673 A | 10/1997 | Ferre et al. |
| 5,697,377 A | 12/1997 | Wittkampf |
| 5,699,799 A | 12/1997 | Xu et al. |
| 5,715,836 A | 2/1998 | Kliegis et al. |
| 5,729,129 A | 3/1998 | Acker |
| 5,752,513 A | 5/1998 | Acker et al. |
| 5,782,762 A | 7/1998 | Vining |
| 5,881,124 A | 3/1999 | Giger et al. |
| 5,891,030 A | 4/1999 | Johnson et al. |
| 5,913,820 A | 6/1999 | Bladen et al. |
| 5,920,319 A | 7/1999 | Vining et al. |
| 5,967,980 A | 10/1999 | Ferre et al. |
| 5,971,767 A | 10/1999 | Kaufman et al. |
| 5,987,960 A | 11/1999 | Messner et al. |
| 6,019,725 A | 2/2000 | Vesely et al. |
| 6,047,080 A | 4/2000 | Chen et al. |
| 6,083,162 A | 7/2000 | Vining |
| 6,138,045 A | 10/2000 | Kupinski et al. |
| 6,151,404 A | 11/2000 | Pieper |
| 6,167,296 A | 12/2000 | Shahidi |
| 6,181,348 B1 | 1/2001 | Geiger |
| 6,201,387 B1 | 3/2001 | Govari |
| 6,233,476 B1 | 5/2001 | Strommer et al. |
| 6,246,784 B1 | 6/2001 | Summers et al. |
| 6,266,551 B1 | 7/2001 | Osadchy et al. |
| 6,332,089 B1 | 12/2001 | Acker et al. |
| 6,346,940 B1 | 2/2002 | Fukunaga |
| 6,366,800 B1 | 4/2002 | Vining et al. |
| 6,381,485 B1 | 4/2002 | Hunter et al. |
| 6,387,092 B1 | 5/2002 | Burnside et al. |
| 6,466,815 B1 | 10/2002 | Saito et al. |
| 6,496,188 B1 | 12/2002 | Deschamps et al. |
| 6,501,848 B1 | 12/2002 | Carroll et al. |
| 6,501,981 B1 | 12/2002 | Schweikard et al. |
| 6,505,065 B1 | 1/2003 | Yanof et al. |
| 6,522,907 B1 | 2/2003 | Bladen et al. |
| 6,526,162 B2 | 2/2003 | Asano et al. |
| 6,535,756 B1 | 3/2003 | Simon et al. |
| 6,578,579 B2 | 6/2003 | Burnside et al. |
| 6,584,174 B2 | 6/2003 | Schubert et al. |
| 6,603,868 B1 | 8/2003 | Ludwig et al. |
| 6,611,793 B1 | 8/2003 | Burnside et al. |
| 6,650,927 B1 | 11/2003 | Keidar |
| 6,651,669 B1 | 11/2003 | Burnside |
| 6,694,163 B1 | 2/2004 | Vining |
| 6,757,557 B1 | 6/2004 | Bladen et al. |
| 6,783,523 B2 | 8/2004 | Qin et al. |
| 6,792,390 B1 | 9/2004 | Burnside et al. |
| 6,829,379 B1 | 12/2004 | Knoplioch et al. |
| 6,850,794 B2 | 2/2005 | Shahidi |
| 6,892,090 B2 | 5/2005 | Verard et al. |
| 6,898,263 B2 | 5/2005 | Avinash et al. |
| 6,909,913 B2 | 6/2005 | Vining |
| 6,920,347 B2 | 7/2005 | Simon et al. |
| 6,925,200 B2 | 8/2005 | Wood et al. |
| 7,006,677 B2 | 2/2006 | Manjeshwar et al. |
| 7,072,501 B2 | 7/2006 | Wood et al. |
| 7,085,400 B1 | 8/2006 | Holsing et al. |
| 7,096,148 B2 | 8/2006 | Anderson et al. |
| 7,149,564 B2 | 12/2006 | Vining et al. |
| 7,167,180 B1 | 1/2007 | Shibolet |
| 7,174,202 B2 | 2/2007 | Bladen et al. |
| 7,179,220 B2 | 2/2007 | Kukuk |
| 7,233,820 B2 | 6/2007 | Gilboa |
| 7,236,558 B2 | 6/2007 | Saito et al. |
| 7,301,332 B2 | 11/2007 | Govari et al. |
| 7,315,639 B2 | 1/2008 | Kuhnigk |
| 7,324,104 B1 | 1/2008 | Bitter et al. |
| 7,336,809 B2 | 2/2008 | Zeng et al. |
| 7,397,937 B2 | 7/2008 | Schneider et al. |
| 7,428,334 B2 | 9/2008 | Schoisswohl et al. |
| 7,452,357 B2 | 11/2008 | Vlegele et al. |
| 7,505,809 B2 | 3/2009 | Strommer et al. |
| 7,517,320 B2 | 4/2009 | Wibowo et al. |
| 7,518,619 B2 | 4/2009 | Stoval, III et al. |
| 7,630,752 B2 | 12/2009 | Viswanathan |
| 7,630,753 B2 | 12/2009 | Simon et al. |
| 7,659,912 B2 | 2/2010 | Akimoto et al. |
| 7,702,153 B2 | 4/2010 | Hong et al. |
| 7,751,865 B2 | 7/2010 | Jascob et al. |
| 7,756,316 B2 | 7/2010 | Odry et al. |
| 7,788,060 B2 | 8/2010 | Schneider |
| 7,792,565 B2 | 9/2010 | Vining |
| 7,805,269 B2 | 9/2010 | Glossop |
| 7,809,176 B2 | 10/2010 | Gundel |
| 7,811,294 B2 | 10/2010 | Strommer et al. |
| 7,822,461 B2 | 10/2010 | Geiger et al. |
| 7,901,348 B2 | 3/2011 | Soper et al. |
| 7,907,772 B2 | 3/2011 | Wang et al. |
| 7,929,014 B2 | 4/2011 | Akimoto et al. |
| 7,951,070 B2 | 5/2011 | Ozaki et al. |
| 7,969,142 B2 | 6/2011 | Krueger et al. |
| 7,985,187 B2 | 7/2011 | Wibowo et al. |
| 8,009,891 B2 | 8/2011 | de Vaan |
| 8,049,777 B2 | 11/2011 | Akimoto et al. |
| 8,055,323 B2 | 11/2011 | Sawyer |
| 8,102,416 B2 | 1/2012 | Ito et al. |
| 8,126,241 B2 | 2/2012 | Zarkh et al. |
| 8,131,344 B2 | 3/2012 | Strommer et al. |
| 8,170,328 B2 | 5/2012 | Masumoto et al. |
| 8,199,981 B2 | 6/2012 | Koptenko et al. |
| 8,200,314 B2 | 6/2012 | Bladen et al. |
| 8,202,213 B2 | 6/2012 | Ito et al. |
| 8,208,708 B2 | 6/2012 | Homan et al. |
| 8,219,179 B2 | 7/2012 | Ganatra et al. |
| 8,257,346 B2 | 9/2012 | Qin et al. |
| 8,267,927 B2 | 9/2012 | Dalal et al. |
| 8,290,228 B2 | 10/2012 | Cohen et al. |
| 8,298,135 B2 | 10/2012 | Ito et al. |
| 8,391,952 B2 | 3/2013 | Anderson |
| 8,417,009 B2 | 4/2013 | Mizuno |
| 8,494,612 B2 | 7/2013 | Vetter et al. |
| 8,509,877 B2 | 8/2013 | Mori et al. |
| 8,672,836 B2 | 3/2014 | Higgins et al. |
| 8,682,045 B2 | 3/2014 | Vining et al. |
| 8,696,549 B2 | 4/2014 | Holsing et al. |
| 8,698,806 B2 | 4/2014 | Kunert et al. |
| 8,700,132 B2 | 4/2014 | Ganatra et al. |
| 8,706,193 B2 | 4/2014 | Govari et al. |
| 8,709,034 B2 | 4/2014 | Keast et al. |
| 8,730,237 B2 | 5/2014 | Ruijters et al. |
| 8,768,029 B2 | 7/2014 | Helm et al. |
| 8,784,400 B2 | 7/2014 | Roschak |
| 8,798,227 B2 | 8/2014 | Tsukagoshi et al. |

(56) References Cited

U.S. PATENT DOCUMENTS

| | | | |
|---|---|---|---|
| 8,798,339 B2 | 8/2014 | Mielekamp et al. | |
| 8,801,601 B2 | 8/2014 | Prisco et al. | |
| 8,819,591 B2 | 8/2014 | Wang et al. | |
| 8,821,376 B2 | 9/2014 | Tolkowsky | |
| 8,862,204 B2 | 10/2014 | Sobe et al. | |
| 10,709,352 B2 | 7/2020 | Costello et al. | |
| 2004/0249267 A1* | 12/2004 | Gilboa | A61B 1/00154 600/424 |
| 2005/0182295 A1 | 8/2005 | Soper et al. | |
| 2008/0183073 A1 | 7/2008 | Higgins et al. | |
| 2009/0012390 A1 | 1/2009 | Pescatore et al. | |
| 2009/0030306 A1 | 1/2009 | Miyoshi et al. | |
| 2009/0048515 A1* | 2/2009 | Suri | A61B 8/12 600/443 |
| 2009/0163810 A1* | 6/2009 | Kanade | A61B 8/0841 600/443 |
| 2010/0030064 A1 | 2/2010 | Averbuch | |
| 2010/0310146 A1 | 12/2010 | Higgins et al. | |
| 2010/0312094 A1 | 12/2010 | Guttman et al. | |
| 2011/0237897 A1 | 9/2011 | Gilboa | |
| 2011/0251607 A1 | 10/2011 | Kruecker et al. | |
| 2012/0203065 A1 | 8/2012 | Higgins et al. | |
| 2012/0249546 A1 | 10/2012 | Tschirren et al. | |
| 2012/0280135 A1 | 11/2012 | Bal | |
| 2012/0287238 A1 | 11/2012 | Onishi et al. | |
| 2013/0165854 A1 | 6/2013 | Sandhu et al. | |
| 2013/0223702 A1 | 8/2013 | Holsing et al. | |
| 2015/0073266 A1* | 3/2015 | Brannan | A61B 5/113 600/424 |
| 2016/0000356 A1 | 1/2016 | Brown et al. | |

OTHER PUBLICATIONS

Canadian Office Action for application No. 2,945,884 dated Feb. 28, 2018 (4 pages).

"Three-dimensional CT-Guided Bronchoscopy With a Real-Time Electromagnetic Position Sensor: A Comparison of Two Image Registration Methods", Stephen B. Solomon, et al.; Chest, American College of Chest Physicians, US, vol. 118, Dec. 1, 2000 (5pages).

Extended European Search Report issued by the European Patent Office corresponding to European Patent Application No. 16195857.4; dated Mar. 13, 2017 (9 pages).

Office Action issued by the Japanese Patent Office corresponding to Japanese Patent Application No. 2016-209580; dated Aug. 31, 2017 with English Translation (7 pages).

Australian Examination Report for application No. 2016250341 dated Oct. 14, 2017 (3 pages).

Japanese Office Action for application No. 2016-209580 dated Jan. 4, 2018 with English translation (5 pages).

Pre-Appeal Examination Report issued by the Japanese Patent Office in Application No. 2016-209680, dated Jul. 20, 2018.

Australian Examination Report No. 3 issued in Appl. No. AU 2016250341 dated Aug. 7, 2018 (3 pages).

Japanese Office Action issued in corresponding Appl. No. JP 2018-088636 dated Mar. 22, 2019, together with English language translation (7 pages).

Japanese Office Action issued in corresponding Appl. No. JP 2016-209580 dated Mar. 29, 2019, together with English language translation (11 pages).

Chinese Office Action issued in corresponding Appl. No. CN 201610951355.8 dated Sep. 2, 2020 (7 pages) together with English language translation retrieved from the Global Dossier (7 pages).

* cited by examiner

METHOD OF USING LUNG AIRWAY CARINA LOCATIONS TO IMPROVE ENB REGISTRATION

CROSS REFERENCE TO RELATED APPLICATION

This application is a continuation of U.S. patent application Ser. No. 15/296,141, filed on Oct. 18, 2016, which claims the benefit of the filing date of provisional U.S. Patent Application No. 62/246,721, filed on Oct. 27, 2015.

INTRODUCTION

The present disclosure relates to bronchial registration and, more particularly, to devices, systems, and methods for automatically registering a three-dimensional bronchial tree model with a patient's real bronchial tree.

BACKGROUND

A common device for inspecting the airway of a patient is a bronchoscope.

Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools, therapeutic instruments can be inserted.

Bronchoscopes, however, are limited in how far they may be advanced through the airways due to their size. Where the bronchoscope is too large to reach a target location deep in the lungs, a clinician may utilize certain real-time imaging modalities such as fluoroscopy. Fluoroscopic images, while useful, present certain drawbacks for navigation as it is often difficult to distinguish luminal passageways from solid tissue. Moreover, the images generated by the fluoroscope are two-dimensional whereas navigating the airways of a patient requires the ability to maneuver in three dimensions.

To address these issues, systems have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB™), system currently sold by Medtronic PLC. The details of such a system are described in commonly assigned U.S. Pat. No. 7,233,820, entitled ENDOSCOPE STRUCTURES AND TECHNIQUES FOR NAVIGATING TO A TARGET IN BRANCHED STRUCTURE, filed on Mar. 29, 2004, by Gilboa, the entire contents of which are incorporated herein by reference.

While the system as described in U.S. Pat. No. 7,233,820 is quite capable, there is always a need for development of improvements and additions to such systems.

SUMMARY

Provided in accordance with the present disclosure is a method of using carina locations to improve registration of a luminal network to a 3D model of the luminal network.

In an aspect of the present disclosure, the method includes generating a 3D model of a luminal network based on images of the luminal network, identifying a target within the 3D model of the luminal network, determining locations of a plurality of carinas in the luminal network proximate the target, displaying guidance for navigating a location sensor within the luminal network, tracking the location of the location sensor while the location sensor is navigated within the luminal network, comparing the tracked locations of the location sensor within the luminal network and the portions of the 3D model representative of open space, displaying guidance for navigating the location sensor a predetermined distance into each lumen originating at the plurality of carinas proximate the target, tracking the location of the location sensor while the location sensor is navigated the predetermined distance into each lumen, and updating the registration of the 3D model with the luminal network based on the tracked locations of the location sensor as it is navigated past the plurality of carinas proximate the target.

In a further aspect of the present disclosure, the luminal network is an airway of a patient.

In yet a further aspect of the present disclosure, the 3D model is a model of the airway of the patient.

In another aspect of the present disclosure, the carinas are used as fiducial markers for identifying the location of the target.

Provided in accordance with the present disclosure is a system of using carina locations to improve registration of a luminal network to a 3D model of the luminal network.

In an aspect of the present disclosure, the comprises a location sensor capable of being navigated within a luminal network inside a patient's body, an electromagnetic field generator configured to detect the location of the location sensor as it is navigated within the luminal network, and a computing device including a processor and a memory storing instructions which, when executed by the processor, cause the computing device to generate a 3D model of the luminal network based on images of the luminal network, identify a target within the 3D model of the luminal network, determine locations of a plurality of carinas in the luminal network proximate the target, display guidance for navigating the location sensor within the luminal network, track the location of the location sensor while the location sensor is navigated within the luminal network, compare the tracked locations of the location sensor within the luminal network and the portions of the 3D model representative of open space, display guidance for navigating the location sensor a predetermined distance into each lumen originating at the plurality of carinas proximate the target, track the location of the location sensor while the location sensor is navigated the predetermined distance into each lumen, and update the registration of the 3D model with the luminal network based on the tracked locations of the location sensor as it is navigated past the plurality of carinas proximate the target.

In a further aspect of the present disclosure, the luminal network is an airway of a patient.

In yet a further aspect of the present disclosure, the 3D model is a model of the airway of the patient.

In another aspect of the present disclosure, the carinas are used as fiducial markers for identifying the location of the target.

Provided in accordance with the present disclosure is a computer-readable storing medium storing instructions which, when executed by a processor, cause a computing device to use carina locations to improve registration of a luminal network to a 3D model of the luminal network.

In an aspect of the present disclosure, the non-transitory computer-readable storing medium stores instructions which, when executed by a processor, cause a computing device to generate a 3D model of a luminal network based on images of the luminal network, identify a target within the 3D model of the luminal network, determine locations of a plurality of carinas in the luminal network proximate the target, display guidance for navigating a location sensor within the luminal network, track the location of the location sensor while the location sensor is navigated within the luminal network, compare the tracked locations of the location sensor within the luminal network and the portions of the 3D model representative of open space, display guidance for navigating the location sensor a predetermined distance into each lumen originating at the plurality of carinas proximate the target, track the location of the location sensor while the location sensor is navigated the predetermined distance into each lumen, and update the registration of the 3D model with the luminal network based on the tracked locations of the location sensor as it is navigated past the plurality of carinas proximate the target.

In a further aspect of the present disclosure, the luminal network is an airway of a patient.

In yet a further aspect of the present disclosure, the 3D model is a model of the airway of the patient.

In another aspect of the present disclosure, the carinas are used as fiducial markers for identifying the location of the target.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Figure 1:
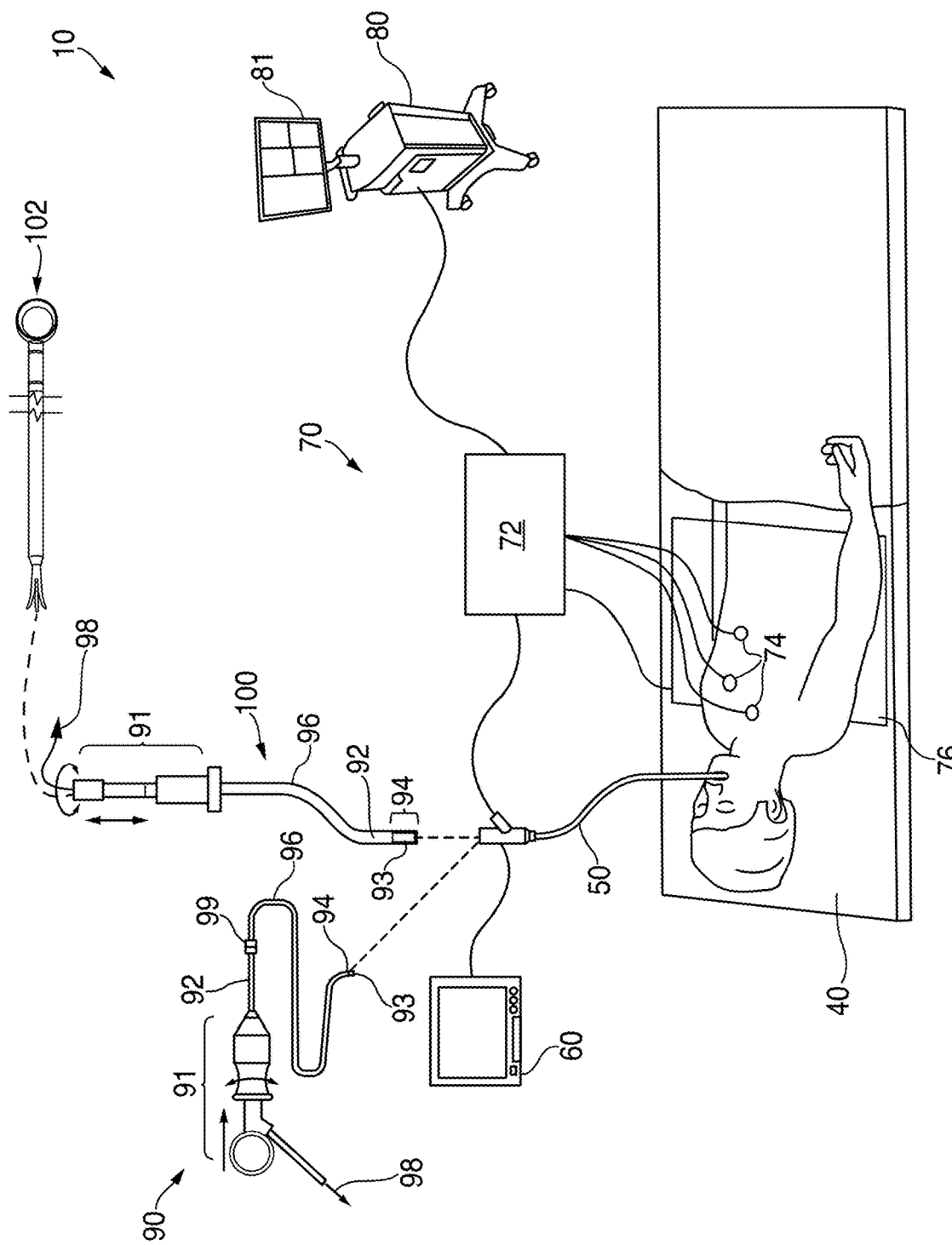
FIG. 1 is a perspective view of an electromagnetic navigation system in accordance with and embodiment of the present disclosure.

The present disclosure is directed to devices, systems, and methods for registering a three-dimensional bronchial tree model (hereinafter referred to as a "3D model") with a patient's airways. Various methods for generating the 3D model and identifying target lesions are envisioned, some of which are more fully described in co-pending U.S. Patent Application Publication Nos. US 2014/0281961, US 2014/0270441, and US 2014/0282216, all entitled PATHWAY PLANNING SYSTEM AND METHOD, filed on Mar. 15, 2013, by Baker, the entire contents of all of which are incorporated herein by reference. Following generation of the 3D model and identification of the target lesions, the 3D model must be registered with the patient's airways. Various methods of manual and automatic registration are envisioned, some of which are more fully described in co-pending U.S. patent application Ser. No. 14/790,581, entitled REAL TIME AUTOMATIC REGISTRATION FEEDBACK, filed on Jul. 2, 2015, by Brown et al., the entire contents of which is incorporated herein by reference.

As is described in more detail below, to further improve registration accuracy between the 3D model and the patient's airways, the clinician may, following automatic registration, perform additional localized registration of the airways surrounding the identified target lesions.

The registration system of the present disclosure, for example, generally includes at least one sensor whose position is tracked within an electromagnetic field. The location sensor may be incorporated into different types of tools, and enables determination of the current location of the tools within a patient's airways by comparing the sensed location in space to locations within the 3D model. The registration facilitates navigation of the sensor or a tool to a target location and/or manipulation of the sensor or tool relative to the target location. Navigation of the sensor or tool to the target location is more fully described in co-pending U.S. patent application Ser. No. 14/753,288, entitled SYSTEM AND METHOD FOR NAVIGATING WITHIN THE LUNG, filed on Jun. 29, 2015, by Brown et al., the entire contents of which is incorporated herein by reference.

Additional features of the ENB system of the present disclosure are described in co-pending U.S. patent application Ser. No. 14/753,229, entitled METHODS FOR MARKING BIOPSY LOCATION, filed on Jun. 29, 2015, by Brown; Ser. No. 14/754,058, entitled INTELLIGENT DISPLAY, filed on Jun. 29, 2015, by Kehat et al.; Ser. No. 14/788,952, entitled UNIFIED COORDINATE SYSTEM FOR MULTIPLE CT SCANS OF PATIENT LUNGS, filed on Jul. 1, 2015, by Greenburg; Ser. No. 14/790,395, entitled ALIGNMENT CT, filed on Jul. 2, 2015, by Klein et al.; Ser. No. 14/725,300, entitled FLUOROSCOPIC POSE ESTIMATION, filed on May 29, 2015, by Merlet; Ser. No. 14/753,674, entitled TRACHEA MARKING, filed on Jun. 29, 2015, by Lachmanovich et al.; Ser. Nos. 14/755,708 and 14/755,721, both entitled SYSTEM AND METHOD FOR DETECTING TRACHEA, filed on Jun. 30, 2015, by Markov et al.; Ser. No. 14/754,867, entitled SYSTEM AND METHOD FOR SEGMENTATION OF LUNG, filed on Jun. 30, 2015, by Markov et al.; Ser. No. 14/790,107, entitled SYSTEM AND METHOD FOR PROVIDING DISTANCE AND ORIENTATION FEEDBACK WHILE NAVIGATING IN 3D, filed on Jul. 2, 2015, by Lachmanovich et al.; and Ser. No. 14/751,257, entitled DYNAMIC 3D LUNG MAP VIEW FOR TOOL NAVIGATION INSIDE THE LUNG, filed on Jun. 26, 2015, by Weingarten et al., the entire contents of all of which are incorporated herein by reference.

Detailed embodiments of such devices, systems incorporating such devices, and methods using the same are described below. However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure. While the example embodiments described below are directed to the bronchoscopy of a patient's airways, those skilled in the art will realize that the same or similar devices, systems, and methods may also be used in other lumen networks, such as, for example, the vascular, lymphatic, and/or gastrointestinal networks.

With reference to FIG. 1, an electromagnetic navigation (EMN) system 10 is provided in accordance with the present disclosure. One such ENM system is the ELECTROMAGNETIC NAVIGATION BRONCHOSCOPY® system currently sold by Medtronic PLC. Among other tasks that may be performed using the EMN system 10 are planning a pathway to target tissue, navigating a positioning assembly to the target tissue, navigating a biopsy tool to the target tissue to obtain a tissue sample from the target tissue using the biopsy tool, digitally marking the location where the tissue sample was obtained, and placing one or more echogenic markers at or around the target.

EMN system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic (EM) field generator 76; a workstation 80 including software and/or hardware used to facilitate pathway planning, identification of target tissue, navigation to target tissue, and digitally marking the biopsy location FIG. 1 also depicts two types of catheter guide assemblies 90, 100. Both catheter guide assemblies 90, 100 are usable with EMN system 10 and share a number of common components. Each catheter guide assembly 90, 100 includes a handle 91, which is connected to an extended working channel (EWC) 96. EWC 96 is sized for placement into the working channel of a bronchoscope 50. In operation, a locatable guide (LG) 92, including an EM sensor 94, is inserted into EWC 96 and locked into position such that sensor 94 extends a desired distance beyond a distal tip 93 of EWC 96. The location of EM sensor 94, and thus the distal end of EWC 96, within an EM field generated by EM field generator 76 can be derived by tracking module 72, and workstation 80. Catheter guide assemblies 90, 100 have different operating mechanisms, but each contain a handle 91 that can be manipulated by rotation and compression to steer distal tip 93 of LG 92 and EWC 96. Catheter guide assemblies 90 are currently marketed and sold by Medtronic PLC under the name SUPERDIMENSION® Procedure Kits. Similarly, catheter guide assemblies 100 are currently sold by Medtronic PLC under the name EDGE™ Procedure Kits. Both kits include a handle 91, EWC 96, and LG 92. For a more detailed description of the catheter guide assemblies 90, 100, reference is made to commonly-owned U.S. Patent Publication Serial No. US 2014/0046315, entitled MICROWAVE ABLATION CATHETER AND METHOD OF UTILIZING THE SAME, filed on Mar. 15, 2013, by Ladtkow et al., the entire contents of which are hereby incorporated by reference.

As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). LG 92 and EWC 96 are selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system, is utilized for performing navigation, although other configurations are also contemplated. Tracking system 70 is configured for use with catheter guide assemblies 90, 100 to track the position of EM sensor 94 as it moves in conjunction with EWC 96 through the airways of the patient, as detailed below.

As shown in FIG. 1, electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes and application 81 which uses data collected by sensors 74 to calculate a patient coordinate frame of reference.

Also shown in FIG. 1 is a catheter biopsy tool 102 that is insertable into catheter guide assemblies 90, 100 following navigation to a target and removal of LG 92. Biopsy tool 102 is used to collect one or more tissue samples from the target tissue. As detailed below, biopsy tool 102 is further configured for use in conjunction with tracking system 70 to facilitate navigation of biopsy tool 102 to the target tissue, tracking of a location of biopsy tool 102 as it is manipulated relative to the target tissue to obtain the tissue sample, and/or marking the location where the tissue sample was obtained.

Although navigation is detailed above with respect to EM sensor 94 being included in LG 92 it is also envisioned that EM sensor 94 may be embedded or incorporated within biopsy tool 102 where biopsy tool 102 may alternatively be utilized for navigation without need of LG 92 or the necessary tool exchanges that use of LG 92 requires. A variety of useable biopsy tools are described in U.S. Provisional Patent Application No. 61/906,732, entitled DEVICES, SYSTEMS, AND METHODS FOR NAVIGATING A BIOPSY TOOL TO A TARGET LOCATION AND OBTAINING A TISSUE SAMPLE USING THE SAME, filed Nov. 20, 2013, U.S. patent application Ser. No. 14/488,754, entitled DEVICES, SYSTEMS, AND METHODS FOR NAVIGATING A BIOPSY TOOL TO A TARGET LOCATION AND OBTAINING A TISSUE SAMPLE USING THE SAME, filed Sep. 17, 2014, and U.S. patent application Ser. No. 14/564,779, entitled DEVICES, SYSTEMS, AND METHODS FOR NAVIGATING A BIOPSY TOOL TO A TARGET LOCATION AND OBTAINING A TISSUE SAMPLE USING THE SAME, filed on Dec. 9, 2014, the entire contents of each of which is incorporated herein by reference and useable with EMN system 10 as described herein.

During procedure planning, workstation 80 utilizes computed tomographic (CT) image data for generating and viewing the 3D model of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. An example of a suitable pathway planning system and method is described in U.S. Patent Application Publication Nos. US 2014/0281961, US 2014/0270441, and US 2014/0282216, all entitled PATHWAY PLANNING SYSTEM AND METHOD, filed on Mar. 15, 2013, by Baker, the entire contents of each of which is incorporated herein by reference.

During navigation, EM sensor 94, in conjunction with tracking system 70, enables tracking of EM sensor 94 and/or biopsy tool 102 as EM sensor 94 or biopsy tool 102 is advanced through the patient's airways.

Figure 2:
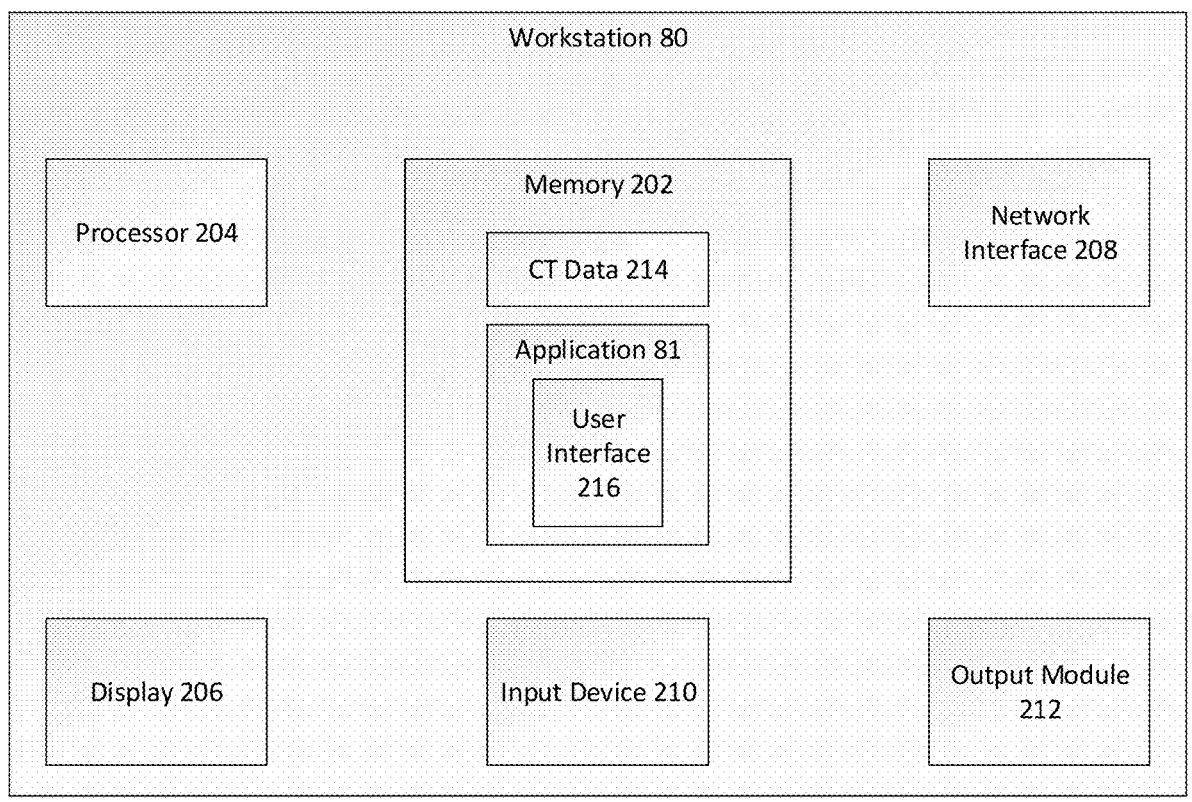
FIG. 2 is a schematic diagram of a workstation configured for use with the system of FIG. 1.

Turning now to FIG. 2, there is shown a system diagram of workstation 80.

Workstation 80 may include memory 202, processor 204, display 206, network interface 208, input device 210, and/or output module 212.

Memory 202 includes any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 202 may store application 81 and/or CT data 214. Application 81 may, when executed by processor 204, cause display 206 to present user interface 216. Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Figure 3:
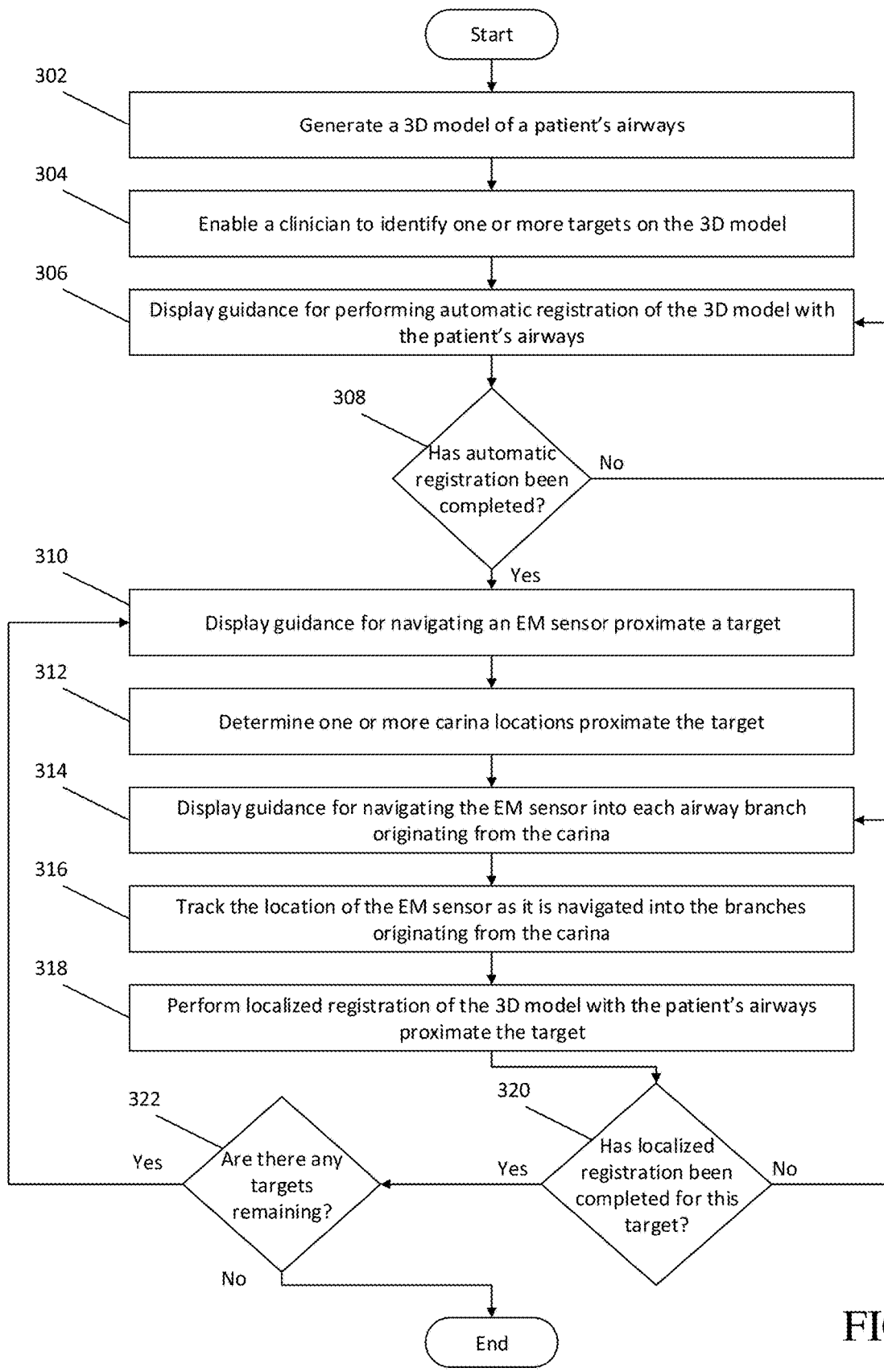
FIG. 3 is a flowchart illustrating a method of using carina locations to improve registration of a luminal network to a 3D model of the luminal network, provided in accordance with and embodiment of the present disclosure.

Referring now to FIG. 3, there is shown a flowchart of an example method for registering the 3D model with a patient's airways. As described above, at step 302, the 3D model is generated prior to the start of the registration process, and, at step 304, the clinician generates a navigation plan based on the 3D model, the navigation plan including one or more targets. Thereafter, the clinician loads the navigation plan into application 81 from memory 202, a USB device, or from network interface 208. The navigation plan may require that all or only some regions of the patient's lungs be registered.

At step 306, application 81 displays guidance for performing automatic registration of the 3D model with the patient's airways, as described above, and in particular as described in co-pending U.S. patent application Ser. No. 14/790,581, entitled REAL TIME AUTOMATIC REGISTRATION FEEDBACK, filed on Jul. 2, 2015, by Brown et al., the entire contents of which is incorporated herein by reference. During registration, the location of EM sensor 94 within the patient's airways is tracked, and a plurality of points denoting the location of EM sensor 94 within the EM field generated by EM generator 76 is stored. At step 308, application 81 determines whether automatic registration has been completed. If no, processing returns to step 306, where further guidance is displayed to complete the automatic registration process. If yes, processing proceeds to step 310.

Figure 4:
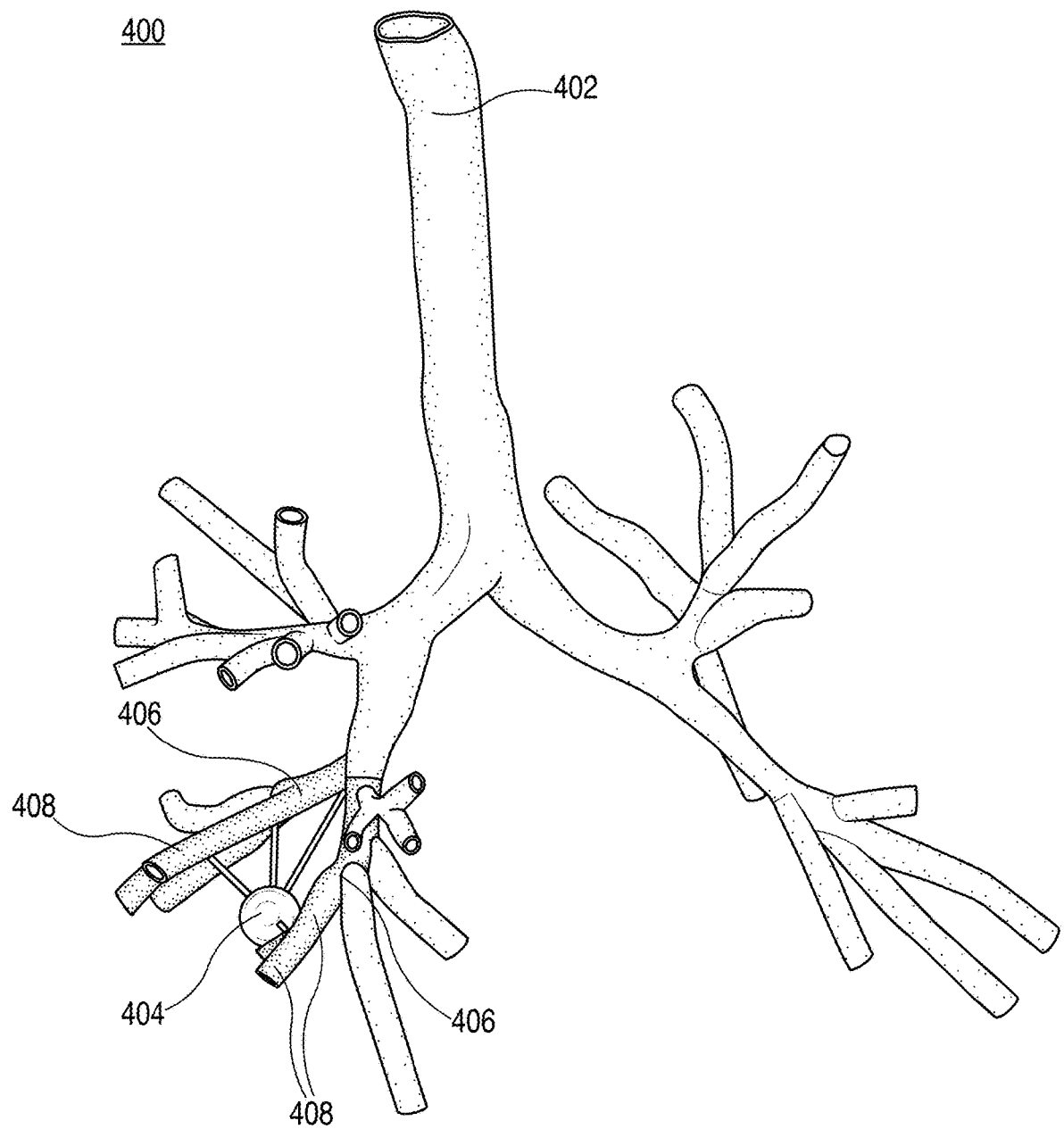
FIG. 4 is a view of a user interface showing carina locations and bifurcations of the luminal network, provided in accordance with an embodiment of the present disclosure.

At step 310, application 81 begins the localized registration process by displaying guidance for navigating EM sensor 94 proximate a target 404. Thereafter, at step 312, application 81 determines one or more carina locations proximate the target. Application 81 determines the carina locations by analyzing the area of the 3D model proximate the target and any bifurcations in the airways. As shown in FIG. 4, a view 400 of the 3D model includes an airway tree 402, target 404, one or more carina 406, and airway branches 408 originating from the bifurcations at the carina 406. For example, application 81 may identify a plurality of carinas 406 approximately evenly spaced in the vicinity of target 404. In embodiments, the carinas may be detected visually by the clinician by viewing a live video feed from a camera located proximate EM sensor 94, for example, in LG 92 or EWC 96. The clinician may match the visually detected carinas with airways depicted on the 3D model.

At step 314, application 81 displays guidance for navigating EM sensor 94 into each airway branch 408 originating from a bifurcation at a carina 406. The clinician follows the displayed guidance to navigate EM sensor 94 in the patient's airways. For example, the guidance may instruct the clinician to navigate EM sensor 94 approximately 1 cm into each airway branch 408. Application 81 tracks the location of EM sensor 94 at step 316 as EM sensor 94 is navigated into the airway branches 408 originating from carina 406 and stores a plurality of points denoting the location of EM sensor 94 within the EM field generated by EM generator 76. Application 81 uses the stored points denoting the location of EM sensor 94 to, at step 318, perform localized registration of the 3D model with the patient's airways proximate the target. For example, localized registration may be performed based on a range of interpolation techniques, such as Thin Plates Splines (TPS) interpolation. In embodiments, TPS interpolation may be used for non-rigid registration of the points denoting the location of EM sensor 94 within the EM field generated by EM generator 76 stored during automatic registration with the 3D model, and may be augmented by additional points stored during localized registration.

Thereafter, at step 320, application 81 determines whether localized registration has been completed for the current target. If no, processing returns to step 314 where further guidance is displayed. If yes, processing proceeds to step 322 where application 81 determines if there are any more targets remaining in the navigation plan for which localized registration has not been performed. If yes, processing returns to step 310, where application 81 displays guidance for navigating EM sensor 94 proximate the next target. If no, the localized registration process is complete, and processing ends.

In addition to using carinas 406 for localized registration, carinas 406 may also be used as fiducial markers for locating target 404. Carinas 406 are particularly useful as fiducial markers because, unlike implanted foreign body markers, carinas 406 cannot migrate.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of registering a luminal network to a 3D model of the luminal network, the method comprising:
    generating a 3D model of a luminal network based on images of the luminal network;
    determining a plurality of locations in the luminal network proximate a target within the luminal network;
    registering the 3D model of the luminal network to the luminal network;
    displaying guidance for navigating a sensor into each of a plurality of lumens originating at one or more bifurcations associated with each of the plurality of locations proximate the target;
    tracking a sensor while the sensor is navigated according to the guidance into each of a plurality of lumens originating at each of the one or more bifurcations associated with the determined plurality of locations;
    locally registering the 3D model of the luminal network to the luminal network proximate the target based on the tracking of the sensor within each of the plurality of lumens; and
    augmenting a registration of the 3D model of the luminal network to the luminal network with a local registration.

2. The method according to claim 1, wherein the luminal network is an airway of a patient.

3. The method according to claim 2, wherein the 3D model is a model of the airway of the patient.

4. The method according to claim 1, wherein at least one of the plurality of locations is used as a fiducial marker for identifying a location of the target.

5. The method according to claim 1, further comprising:
    using thin plate spline interpolation to non-rigidly register the 3D model of the luminal network to the luminal network; and
    augmenting the non-rigid registration of the 3D model of the luminal network to the luminal network with the local registration.

6. The method according to claim 1, further comprising using thin plate spline interpolation to locally register the 3D model of the luminal network to the luminal network proximate the target.

7. The method according to claim 1, further comprising:
    determining if the local registration of the 3D model of the luminal network to the luminal network proximate the target is complete; and
    displaying further guidance for navigating the sensor into each of the plurality of lumens originating at the one or more bifurcations associated with each of the plurality of locations proximate the target if it is determined that the local registration proximate the target is not complete.

8. The method according to claim 1, further comprising:
    determining if the local registration of the 3D model of the luminal network to the luminal network proximate at least one additional target is complete; and
    displaying further guidance for navigating the sensor into each of a plurality of lumens originating at the one or more bifurcations associated with each of the plurality of locations proximate the at least one additional target if it is determined that the local registration proximate the at least one additional target is not complete.

9. The method according to claim 1, further comprising:
    storing, in a memory of a computing device, the registration of the 3D model of the luminal network to the luminal network; and
    augmenting the stored registration of the 3D model of the luminal network to the luminal network with the local registration.

10. A system for registering a luminal network to a 3D model of the luminal network, the system comprising:
    a sensor configured to be navigated within a luminal network inside a patient's body; and
    a computing device including a processor and a memory storing instructions which, when executed by the processor, cause the computing device to:
        generate a 3D model of the luminal network based on images of the luminal network;
        determine a plurality of locations in the luminal network proximate a target;
        register the 3D model of the luminal network to the luminal network;
        track the sensor while the sensor is navigated according to the guidance into each of a plurality of lumens originating at one or more bifurcations associated with each of the plurality of locations proximate the target;
        locally register the 3D model of the luminal network to the luminal network proximate the target based on the tracking of the sensor within each of the plurality of lumens; and
        augment a registration of the 3D model of the luminal network to the luminal network with a local registration.

11. The system according to claim 10, wherein the luminal network is an airway of a patient.

12. The system according to claim 11, wherein the 3D model is a model of the airway of the patient.

13. The system according to claim 10, wherein at least one of the plurality of locations is used as a fiducial marker for identifying a location of the target.

14. A non-transitory computer-readable storage medium storing instructions which, when executed by a processor, cause the computing device to:
    generate a 3D model of a luminal network based on images of the luminal network;
    determine locations of a plurality of bifurcations in the luminal network proximate a target;
    register the 3D model of the luminal network to the luminal network;
    track a sensor while the sensor is navigated according to the guidance into each of a plurality of lumens originating at each of the plurality of bifurcations proximate the target;

locally register the 3D model of the luminal network to the luminal network proximate the target based on the tracking of the sensor within each of the plurality of lumens; and augment a registration of the 3D model of the luminal network to the luminal network with a local registration.

15. The non-transitory computer-readable storage medium according to claim 14, wherein the luminal network is an airway of a patient.

16. The non-transitory computer-readable storage medium according to claim 15, wherein the 3D model is a model of the airway of the patient.

17. The non-transitory computer-readable storage medium according to claim 14, wherein at least one of the plurality of bifurcations is used as a fiducial marker for identifying a location of the target.

18. The non-transitory computer-readable storage medium according to claim 14, wherein the instructions, when executed by the processor, cause the computing device to display guidance for navigating the sensor into each of the plurality of lumens originating at each of the plurality of bifurcations proximate the target.

\* \* \* \* \*